United States Patent [19]

MacKay et al.

[11] 4,020,081
[45] Apr. 26, 1977

[54] CERTAIN BENZOXAZOLES AND THE USE THEREOF AS METAL EXTRACTANTS

[75] Inventors: Kenneth D. MacKay, Circle Pines; Edgar R. Rogier, Hopkins, both of Minn.

[73] Assignee: General Mills Chemicals, Inc., Minneapolis, Minn.

[22] Filed: Oct. 25, 1974

[21] Appl. No.: 518,011

[52] U.S. Cl. .................. 260/307 D; 260/559 S; 260/575; 260/645; 423/24; 423/139; 423/658.5
[51] Int. Cl.² ....................... C07D 263/56
[58] Field of Search ................. 260/307 D

[56] References Cited
UNITED STATES PATENTS 2,995,540  8/1961  Duennenberger et al. ....... 260/45.8
3,669,979  6/1972  Freyermuth ..................... 260/304

FOREIGN PATENTS OR APPLICATIONS 2,010,635  2/1970  France

*Primary Examiner*—Raymond V. Rush

*Attorney, Agent, or Firm*—Gene O. Enockson; Patrick J. Span

[57] ABSTRACT

Benzoxazoles having the structure

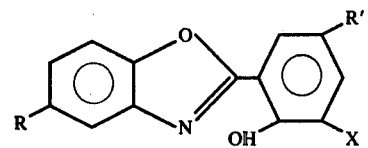

where R is hydrogen or an alkyl group having from 1 to 20 carbon atoms, R' is hydrogen, chlorine or an alkyl group containing from 1 to 20 carbon atoms, X is H or Chlorine and the total number of carbon atoms in R and R' is 6 to 40 with the proviso that one of R and R' must be an alkyl group of at least 6 carbon atoms. The benzoxazoles are useful in a process of recovering metal values, particularly copper and nickel, from aqueous solutions thereof.

11 Claims, No Drawings

CERTAIN BENZOXAZOLES AND THE USE THEREOF AS METAL EXTRACTANTS

FIELD OF THE INVENTION

This invention relates to certain new benzoxazoles and to the use of the same metal extractants.

BACKGROUND OF INVENTION

Liquid ion exchange recovery of metal values from aqueous solutions is rapidly reaching extensive commercial acceptance. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should meet a number of criteria. In the first instance, the reagent must complex with or react with a metal or group of metals. It is also desirable that the reagent show preference for a single metal where the aqueous starting solutions contain a number of metal values. The reagent should also, desirably, complex or react quantitatively with the metal under the extraction conditions. Additionally, the reagent, as well as the resulting metal complex, must exhibit satisfactory solubility in practical solvents. Further, the reagent-metal reaction must be reversible so that the metal can be stripped. For economic reasons, the reagent must be acceptably stable so that it can be recycled repeatedly. Also, it should be essentially water insoluble to prevent significant loss into the aqueous phase. Furthermore, the reagent should not cause or stabilize emulsions. And, of course, the cost of the reagent should be such that the liquid ion exchange process can be operated at a profit. Very few compounds have, as yet, found significant commercial acceptance.

Certain benzoxazoles are known. These are generally prepared by condensation of a salicylic acid compound, such as, salicylamide with an aminophenol. This is generally described in The Journal of Physical Chemistry, Vol. 74, No. 26, (1970), pp. 4473–4480. In U.S. Pat. No. 2,995,540, there are disclosed certain benzoxazoles which are useful for protection against ultra-violet radiation. These benzoxazoles contain lower alkyl groups such as methyl groups. In Analytica Chemica Acta, Vol. 11, (1954), pp. 301–308, there is reported a study of the stability of chelates of 2-(o-hydroxyphenyl)-benzimidazole and analogous reagents, one of such analogous reagents being 2-(o-hydroxyphenyl)-benzoxazole.

SUMMARY OF INVENTION

The new benzoxazole compounds of this invention have been found to be effective extractants of copper and nickel from ammoniacal aqueous solutions. They are effective in solutions containing, in addition to copper and nickel, other metals such as cobalt and zinc. The extractant offers the following advantages:
1. High copper loadings
2. Good selectivity
3. Ease of acid stripping Our new compounds have acceptable solubility in practical, commercially usable solvents. The metal complexes thereof alos have acceptable solubility. Further, the new compounds extract satisfactory amounts of copper and/or nickel.

The new benzoxazole compounds of the inention can be defined structurally as follows:

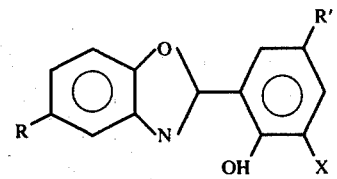

where R is hydrogen or an alkyl group having from 1 to 20 carbon atoms, R' is hydrogen, chlorine or an alkyl group containing from 1 to 20 carbon atoms, X is H or chlorine and the total number of carbon atoms in R and R' is 6 to 40 with the proviso that one of R and R' must be an alkyl group of at least 6 carbon atoms. Preferably R is an alkyl group containing at least 6 carbon atoms. The benzoxazoles are useful in a process of recovering metal values, particularly copper and nickel, from aqueous solutions thereof. For nickel extractions, it is preferred that both R' and X are chlorine. Also, it is especially preferred that R is an alkyl group containing 9 or more carbon atoms.

The new compounds are prepared in the known manner by condensation of a salicylamide with an aminophenol at temperatures of about 200° to 240° C. The aminophenol is prepared by nitration of a phenol followed by hydrogenation. The preparation sequence can be seen as follows:

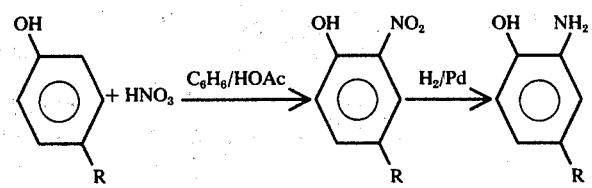

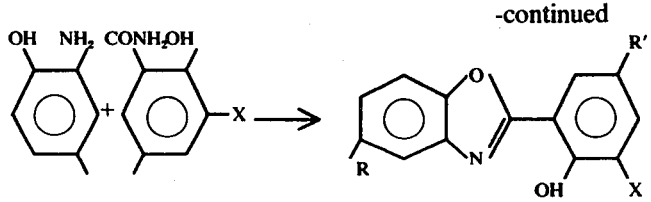

where R as previously defined.

The compound preparations can be further described by use of the following examples which are to be considered as illustrating preferred embodiments without being limiting.

EXAMPLE I

A. Preparation of 2-Nitro-4-dodecylphenol

A mixture of 545 g. (2.08 moles) of p-dodecylphenol, 700 ml of benzene, and 500 ml of glacial acetic acid was placed in a 5 liter three-neck flask fitted with a dropping funnel, thermometer, and mechanical stirrer. The mixture was cooled to 0°–5° C in an ice-salt bath and kept at that temperature during nitration. With stirring, 225 ml of 70% nitric acid was added slowly over 5½ hours.

After the addition was complete, the reaction mixture was placed in a separatory funnel and washed three times with water and twice with saturated aqueous sodium chloride. In order to obtain neutrality in the aqueous phase, solid sodium bicarbonate was added accompanied by carbon dioxide evolution. After phase separation, the organic was stripped of volatiles by distillation under reduced pressure. distillation distilation gave 422.3 g. (1.38 mole) of 2-nitro-4-dodecylphenol, boiling point of 170°–187° C (1–3 mm). The structure of the product was confirmed by infrared, nuclear magnetic resonance (nmr), and mass spectral analyses.

B. Preparation of 2-Amino-4-dodecylphenol

A mixture of 61.4 g. (0.2 mole) of 2-nitro-4-dodecylphenol and 1 g. of 5% of palladium on carbon slurried in 100 ml of 95% ethanol was placed in a 250 ml hydrogenation bottle. The bottle was stopped under an atmosphere of 45 psi of hydrogen and shaken at room temperature. The hydrogen was replenished during reaction. After 4 hours the hydrogen uptake was complete. The mixture then was filtered through a sintered glass funnel and the filtrate was stripped of solvent under reduced pressure. The yield of product, 2-amino-4-dodecylphenol, was quantitative. Infrared, nuclear magnetic resonance (nmr) and gas liquid chromatography (glc) analyses confirmed its structure and purity.

C. Preparation of 2-(2-Hydroxyphenyl)-5-dodecylbenzoxazole

A three-neck flask fitted with a thermometer, mechanical stirrer and condenser with Dean-Stark trap was charged with 692.5 g. (2.5 moles) of 2-amino-4-dodecylphenol and 411 g. (3.0 moles) of salicylamide. The mixture was heated with stirring to 220° C. After 6 hours of the heating, the collection of water in the Dean-Stark trap ceased. At that point, the reaction mixture was cooled to room temperature and about 3 liters of cyclohexane was added. The mixture was then filtered and the filtrate was stripped of volatiles under reduced pressure. The yield of residue was 741.5 g. (2.0 moles). Infrared and nuclear magnetic resonance (nmr) analyses confirmed the structure of the product as 2-(2-hydroxyphenyl)-5-dodecylbenzoxazole, a dark oil. A gas liquid chromatography (glc) analysis indicated the product was 95+% pure.

EXAMPLE II

A. Preparation of 2-Nitro-4-hexylphenol

A mixture of 35.6 g. (0.2 mole) of 4-hexylphenol, 70 ml of benzene, and 50 ml of glacial acetic acid was placed in a three-neck flask fitted with a dropping funnel, thermometer, and mechanical stirrer. The mixture was cooled to 0°–5° C in an ice-salt bath and kept at that temperature during the addition of 12 ml of 70% nitric acid, which was added over a 3 hour period. After the addition was complete, the mixture was stirred at room temperature for one hour at which time 100 ml of water was added to the mixture. The contents of the reaction flask then were transferred to a separatory funnel and the layers were separated. The organic phase was washed with consecutive portions of water until the pH of the wash was 4. The organic phase was removed and dried over anhydrous sodium sulfate. The volatiles then were stripped by evaporation under reduced pressure. Further distillation gave 34.2 g. of 2-nitro-4-hexylphenol, boiling point (bpt) of 180°–195° (.4 mm). The structure and purity of the product were confirmed by infrared analysis.

B. Preparation of 2-(2-Hydroxyphenyl)-5-hexylbenzoxazole

A mixture of 22.8 g. (0.102 mole) of 2-nitro-4-hexylphenol and 0.25 g. of 5% palladium on carbon slurried in 150 ml of 95% ethanol was placed in a 250 ml hydrogenation bottle. The bottle was stoppered under an atmosphere of 45 psi of hydrogen and shaken at room temperature. The hydrogen was replenished during reaction. After three hours hydrogen uptake was complete. The mixture then was filtered through a sintered glass funnel and the filtrate was stripped of solvent under reduced pressure. The distillation residue then was added to a three neck flask fitted with a thermometer, mechanical stirrer, and a condenser with a Dean-Stark trap charged with 13.7 g. (0.1 mole) of salicylamide. The mixture was heated with stirring to 200° C and held at 200°–220° C for 4 hours. The reaction mixture then was cooled to room temperature and 150 ml of cyclohexane were added. The resulting mixture was filtered and the cyclohexane was removed from the filtrate by distillation under reduced pressure. The distillation residue weighed 22.4 g. and infrared analysis confirmed the composition as 2-(2-hydroxyphenyl)-5-hexylbenzoxazole.

EXAMPLE III

A. Preparation of 5-Octylsalicylamide

A 1 liter Parr autoclave was charged with 88.4 g. (0.33 mole) of methyl-5-octylsalicylate in 300 ml of toluene and sealed. Then 35 g. (2.06 moles) of anhydrous ammonia was added. The autoclave then was heated with stirring to 100° C (300 psi) for 16 hours. After cooling to room temperature, a precipitate was present in the autoclave. It was collected by filtration of the slurry.

The filtration residue was recrystallized from acetoneheptane giving 26.0 g. of solids. The acetone then was evaporated from the mother liquors leaving an additional 33.7 g. of solids. The two fractions were combined and slurried in a solution of dichloromethane and heptane at 40° C. The mixture then was heated until the dichloromethane had evaporated. After cooling to room temperature, 55.6 g. of product were collected. The structure and purity of 5-octylsalicylamide were confirmed by infrared and gas chromatographic analysis.

B. Preparation of 2-(2-Hydroxy-5-octylphenyl-5-dodecylbenzoxazole

A three-neck flask fitted with a thermometer, mechanical stirrer, and condenser with Dean-Stark trap was charged with 49 g. (0.2 mole) of 2-amino-4-dodecylphenol and 54.7 g. (0.2 mole) of 5-octysalicylamide. The mixture was heated with stirring at 220°–230° C for 36 hours. After cooling to room temperature, no purification was necessary. Infrared, gas chromatographic, and mass spectral analysis confirmed the structure and purity of 2-(2-hydroxy-5-octylphenyl)-5-dodecylbenzoxazole.

EXAMPLE IV

A. Preparation of 3,5-Dichlorosalicylamide

A 1 liter Parr autoclave was charged with 221 g. (1 mole) of methyl 3,5-dichlorosalicylate and 140 g. (8 moles) of anhydrous ammonia. The mixture was stirred at 25° C for 24 hours. After venting excess ammonia, the product was ground to a fine powder and triturated with boiling chloroform. The mixture was filtered while hot and the residue weighed 152 g. Analysis by infrared, gas chromatography, and nuclear magnetic resonance confirmed that the product was 3,5-dichlorosalicylamide.

B. Preparation of 2-(2-Hydroxy-3,5-dichlorophenyl) 5-dodecylbenzoxazole

A three-neck flask fitted with a thermometer, mechanical stirrer, and condenser with Dean-Stark trap was charged with 193.9 g. (0.7 mole) of 2-amino-4-dodecylphenol and 144.2 g. (0.7 mole) of dichlorosalicylamide. The mixture was heated with stirring at 230° C for 8 hours. After cooling to room temperature, about 1 liter of hexane was added and the resulting mixture was filtered to remove traces of hexane insoluble residues. The hexane was evaporated under reduced pressure leaving 254.1 g. of product which was identified by infrared, nuclear magnetic resonance, and mass spectroscopy as 2-(2-hydroxy-3,5-dichlorophenyl)-5-dodecylbenzoxazole.

EXAMPLE V

A. Preparation of 2-Nitro-4-nonylphenol

A mixture of 438 g. (2.0 moles) of 4-nonylphenol, 700 ml of benzene, and 500 ml of glacial acetic acid was placed in a three-neck flask fitted with a dropping funnel thermometer, and mechanical atirrer. The mixture was cooled to 0°–5° C in an ice-salt bath. Then 142 ml of 70% nitric acid was added over a period of 6½ hours at such a rate that the temperature did not rise above 5° C. After the addition was complete, the mixture was stirred an additional hour.

Water was added to the reaction flask and the mixture was transferred to a separatory funnel. The organic phase was washed with successive portions of water until the pH of the water phase was 4. The organic phase was dried over anhydrous magnesium sulfate and the solvents were stripped by evaporation under reduced pressure. The residue then was distilled and gave fractions, which were shown to be 2-nitro-4-nonylphenol by infrared and nuclear magnetic resonance analysis (bpt 114°–135° C, 0.15–0.5mm).

B. Preparation of 2-(2-hydroxyphenol)-5-nonylbenzoxazole

A mixture of 66.3 g. (0.2 mole) of 2-nitro-4-nonylphenol and 0.5 g. of 5% palladium on carbon slurried in 100 ml of 95% ethanol was placed in 250 ml hydrogenation bottle. The bottle was stoppered under an atmosphere of 45 psi of hydrogen and shaken at room temperature. The hydrogen was replenished during the reaction. After 4 hours hydrogen uptake was complete. The mixture then was filtered through a sintered glass funnel and the filtrate was stripped of solvent under reduced pressure. The distillation residue then was added with 137 g. (0.27 mole of salicylamide into a three-neck flask fitted with a thermometer, mechanical stirrer, and condenser with a Dean-Stark trap. The mixture then was heated with stirring at 220° C for 3 hours. After cooling to room temperature, 250 ml of hexane was added with stirring. The resulting mixture was filtered and the filtrate was warmed to 40° C under reduced pressure. The product weighed 78.8 g. and infrared analysis indicated that it was 2-(2-hydroxyphenyl)-5-nonylbenzoxazole.

As indicated above, the new compounds set forth herein are useful for the extraction of metals from aqueous solutions which extraction process also forms part of the invention. The compounds are particularly effective as extractants for copper from ammoniacal solutions thereof.

In the extraction recovery process, the new benzoxazoles are dissolved in an organic solvent boiling above about 150° C and the solution is contacted with the aqueous metal containing solution to form a complex of the metal and the benzoxazole. The organic phase is then separated from the aqueous phase and the metal values are stripped from the organic phase. As such, the new benzoxazoles of the present invention are further characterized as having a solubility in such organic solvents of at least 2% by weight and the metal complexes formed therefrom also have this minimum solubility.

The high boiling organic solvents are essentially water immiscible and are preferably aliphatic hydrocarbons such as the petroleum derived liquid hydrocarbons, either straight or branched, such as kerosene (a preferred brand being Napoleum 470), fuel oil, etc. In addition to the simple hydrocarbon solvents, chlorinated hydrocarbons may also, desirably, be used. Accordingly, both the unsubstituted and the chlorinated solvents are contemplated by the term "liquid hydrocarbon".

In the process of the invention, the new benzoxazoles are dissolved in the organic solvent in an amount sufficient to extract at least some of the metal values from their aqueous solution. Preferably, the benzoxazoles will be used in amounts of about 2 to 20% by weight based on the weight of the organic solvent.

The aqueous solution containing the metal values preferably has a pH above 7.0 and the invention is of particular value with metal (i.e. copper) containing solutions having a pH above 7.5 up to about 10.5.

The phase ratios can vary widely since the contacting of any quantity of the benzoxazole solution with the metal containing aqueous phase will result in extraction of metal values into the organic phase. However, the organic: aqueous phase ratios are preferably in the range of 20:1 to 1:20 and even more preferably of 5:1 to 1:5 for commercial practicality. For practical purposes, the extractions (and strippings) are normally carried out at ambient temperatures and pressures. The entire process can be carried out continuously with the stripped organic solvent solution being recycled for contacting further quantities of metal containing solutions.

The loaded organic is preferably stripped using aqueous acid stripping mediums such as aqueous sulfuric acid (i.e. 25–150 g/1 $H_2SO_4$). The metal values are then desirably recovered from the aqueous stripping medium by electrolysis. The loaded organic: aqueous stripping phase ratios can also vary widely. However, the over-all object of the process is to provide a metal containing stripping solution wherein the metal is present in higher concentrations than in the starting aqueous solution. Accordingly, the loaded organic aqueous stripping phase ratio will preferably be in the range of 1:1 to 1:10.

The following examples illustrate preferred embodiments of the extraction process of the present invention without being limiting. In such examples, extractions and strippings were performed by preparing separately the organic and aqueous solutions at the concentrations indicated. The organic and aqueous solutions were then added, at the volume ratios (O/A) indicated to a bottle which was immediately sealed. The bottle was placed on a mechanical shaker and shaken for one hour (unless otherwise indicated) after which the contents were transferred to a separatory funnel. When phase separation was complete, both the organic and aqueous phases were sampled and analyzed for metal concentration by atomic absorption spectrometry. Kinetic experiments were performed by placing the aqueous phase of known solute concentration into a square box and stirring the solution under conditions of high shear. An equal volume of organic phase of known concentration (reagent and/or solute) is then added at once. Aliquots of the vigorously stirred mixture are then taken at the designated time intervals and transferred to separatory funnels. After phase separation, each phase is sampled and analyzed by atomic absorption spectrometry for metal concentration. The term "w/v" in the examples means that a prescribed weight of the benzoxazole extractant — i.e. 3.8 g. — is made up to a prescribed volume by addition of the solvent — i.e. to 100 ml. — to yield the % weight/volume — i.d. 3.8% w/v. Also, in the examples, the starting aqueous phases all contained the metal values indicated in the form of the sulfates thereof — i.e. $CuSO_4$.

EXAMPLE VI

In this example, the extraction of copper with the 2-(2-hydroxyphenyl)-5-dodecylbenzoxazole of Example I was studied. The results may be seen from the following Table 1 which shows:

a. The reagent loaded 19.5 g/l of copper without precipitation at a reagent concentration of about 19% w/v.

b. No ammonia was carried into the organic phase during the copper extraction, nor did the compound extract ammonia in the absence of copper.

TABLE 1

| | Extraction of Copper | |
|---|---|---|
| O/A | Organic Cu++ g/l | Aqueous Cu++ g/l |
| Feed[1] | — | 3.10 |
| 2/1 | 1.53 | 0.00 |
| 1/1 | 2.92 | 0.19 |
| 1/2 | 2.99 | 1.60 |
| Feed[2] | — | 10.6 |
| 1/2 | 18.1 | 0.29 |
| Feed[2] | 18.1 | 10.6 |
| 1/2 | 19.5 | — |
| Feed[2] | 19.5 | 10.6 |
| 1/2 | 19.5 | — |

[1]The organic was 3.8% w/v of the product of Example I in Napoleum 470. The aqueous contained about 5 g/l $NH_3$ and 7 g/l $(NH_4)_2CO_3$.
[2]The organic was 19% w/v of the product of Example I in Napoleum 470. The aqueous contained about 9 g/l $NH_3$ and 50 g/l $(NH_4)_2CO_3$. The loaded organic from the first Feed[2] extraction was used in the next extraction and that from the second in the third extraction.

EXAMPLE VII

In this Example the copper-nickel kinetics were studied using the compound of Example I. The organic consisted of 3.8% w/v in Napoleum 470 and an organic to aqueous ratio (O/A) of 1:1 was used. The aqueous copper solution contained 3.2 g/l copper, 5 g/l $NH_3$ and 7/g/l $(NH_4)_2CO_3$. The study was conducted in the following manner:

The data for the extraction of copper and nickel as a function of time (kinetics) are presented in the following Tables 2 and 3 which indicate that copper is extracted more rapidly than nickel.

TABLE 2

| | Rate of Copper Extraction | |
|---|---|---|
| Time | Organic Cu++ g/l | Aqueous Cu++ g/l |
| 15 sec | 2.82 | 0.41 |
| 30 sec | 2.90 | 0.33 |
| 60 sec | 2.95 | 0.28 |
| 2 min | 2.97 | 0.25 |
| 5 min | 3.02 | 0.27 |
| 10 min | 2.98 | 0.27 |

TABLE 3

| | Rate of Nickel Extraction | |
|---|---|---|
| Time | Organic Ni++ g/l | Aqueous Ni++ g/l |
| 15 sec | — | 2.68 |
| 30 sec | 0.26 | 2.56 |
| 60 sec | 0.38 | 2.47 |
| 2 min | 0.49 | 2.38 |
| 5 min | 0.82 | 2.02 |

TABLE 3-continued

| | Rate of Nickel Extraction | |
|---|---|---|
| Time | Organic Ni++ g/l | Aqueous Ni++ g/l |
| 10 min | 1.36 | 1.42 |

EXAMPLE VIII

In this example the results on copper extraction from synthetic leach solutions of varying ammonia and carbonate concentrations using the benzoaxazole of Example I were studied. The aqueous copper solution contained about 13.1 g/l copper. The organic phase consisted of 19% w/v (0.5M) of the benzoxazole of Example I in Napoleum 470. An O/A ratio of 1:1 was employed.

TABLE 4

Extraction of Copper as a Function of Ammonia Concentration in the Aqueous Phase

| $[NH_3]^1$ g/l | $[(NH_4)_2CO_3]$ g/l | % Extraction |
|---|---|---|
| 25.0 (1.5M) | 50 (0.5M) | 99.9 |
| 27.0 (1.6M) | 50 (0.5M) | 99.8 |
| 37.9 (2.2M) | 50 (0.5M) | 98.6 |
| 60.0 (3.5M) | 50 (0.5M) | 93.8 |
| 30.9 (1.8M) | 100 (1.0M) | 100.0 |
| 40.0 (2.4M) | 100 (1.0M) | 99.6 |
| 60.2 (3.5M) | 100 (1.0M) | 95.3 |
| 98.4 (5.8M) | 100 (1.0M) | 78.7 |

[1]Total analysable ammonia.

EXAMPLE IX

In this example the acid stripping of a heavily loaded organic copper solution (19.5 g/l copper, 0.0 g/l $NH_3$) of the benzoxazole of Example I in Napoleum 470 (19% w/v) was studied. An O/A ratio of 1:1 was employed. The stoichiometry for stripping 19.5 g/l of copper requires 30 g/l of sulfuric acid. More lightly loaded solutions would require less acid for stripping. The results can be seen from the following Table 5.

TABLE 5

Stripping of Copper

| Strip Solution | | Stripped Organic |
|---|---|---|
| $H_2SO_4$ g/l | Cu++ g/l | Cu++ g/l |
| 25 | 40 | 11.0 |
| 25 | 0 | 7.9 |
| 50 | 40 | 6.9 |
| 50 | 0 | 5.0 |
| 75 | 40 | 1.0 |
| 75 | 0 | 0.6 |

EXAMPLE X

The selectivity of the benzoxazole of Example I for copper over nickel and zinc is depicted in the following Table 6.

TABLE 6

Selectivity of 2-(2-Hydroxyphenyl)-5-Dodecylbenzoxazole[1] for Copper, Nickel, and Zinc

| | Organic | | Aqueous | |
|---|---|---|---|---|
| O/A | Cu++ | Ni++ | Cu++ | Ni++ |
| Feed[2] | | | 1.54 g/l | 1.40 g/l |
| 1/2 | 2.96 g/l | 0.38 g/l | 0.07 g/l | 1.25 g/l |
| 1/1 | 1.59 g/l | 0.55 g/l | 0.00 g/l | 0.91 g/l |
| 2/1 | 0.83 g/l | 0.44 g/l | 0.00 g/l | 0.55 g/l |
| | Cu++ | Zn++ | Cu++ | Zn++ |

TABLE 6-continued

Selectivity of 2-(2-Hydroxyphenyl)-5-Dodecylbenzoxazole[1] for Copper, Nickel, and Zinc

| | Organic | | Aqueous | |
|---|---|---|---|---|
| Feed[2] | | | 1.56 g/l | 1.55 g/l |
| 1/2 | 2.96 g/l | 0.08 g/l | 0.02 g/l | 1.74 g/l |
| 1/1 | 1.62 g/l | 0.13 g/l | 0.00 g/l | 0.47 g/l |
| 2/1 | 0.83 g/l | 0.19 g/l | 0.00 g/l | 0.98 g/l |

[1]About 4% w/v (0.1M) in Napoleum 470.
[2]Contained about 5 g/l $NH_3$ and 7 g/l $(NH_4)_2CO_3$.

EXAMPLE XI

In the same manner as in Examples VI – IX, similar studies were made using the 2-(2-hydroxy-5-octyl)-5-dodecylbenzoxazole of Example III. The results can be seen from the following Tables 7 – 11.

TABLE 7

Extraction of Nickel from Ammoniacal Solution[1] with the Benzoxazole of Example III[2]

| O/A | Extraction Time Hours | Organic Ni++ g/l | Aqueous Ni++ g/l |
|---|---|---|---|
| | | | 2.64 |
| 1/5 | 1 | 0.58 | 2.75 |
| 1/2 | 1 | 0.41 | 2.65 |
| 1/1 | 1 | 0.30 | 2.58 |
| 1/1 | 24 | 0.92 | 1.81 |
| 2/1 | 1 | 0.25 | 2.40 |
| 5/1 | 1 | 0.19 | 2.07 |

[1]Contained about 7 g/l $NH_3$ and 7 g/l $(NH_4)_2CO_3$.
[2]About 4.9% w/v in Napoleum 470.

TABLE 8

Extraction of Copper from Aqueous Ammoniacal Solutions[1] with the Benzoxazole of Example III

| | Organic Cu++ g/l | Aqueous Cu++ g/l |
|---|---|---|
| Feed[2] | 0.0 | 13.1 |
| O/A = 1/1 | 9.3 | 0.008 |
| Feed[3] | 0.0 | 13.1 |
| O/A = 1/1 | 13.9 | 0.06 |
| Feed[3] | 13.9 | 13.1 |
| O/A = 1/1 | 18.0 | — |
| Feed[3] | 18.0 | 13.1 |
| O/A = 1/1 | 18.3 | — |

[1]Contained about 9 g/l $NH_3$ and 50 g/l $(NH_4)_2CO_3$.
[2]Concentration of Compound of Example III in Napoleum 470 was = 12.3% w/v (0.25M).
[3]Concentration of Compound of Example III in Napoleum 470 was 24.5% w/v (0.5M). The loaded organic was successively used in the second and third extraction.

TABLE 9

Extraction of Copper[1] as a Function of Ammonia Concentration with the Benzoxazole of Example III[1]

| $[NH_3]^3$ g/l | $(NH_4)_2CO_3$ g/l | % Extraction |
|---|---|---|
| 25.0 (1.5M) | 50 (0.5M) | 99.6 |
| 27.0 (1.6M) | 50 (0.5M) | 99.3 |
| 37.9 (2.2M) | 50 (0.5M) | 95.7 |
| 60.0 (3.5M) | 50 (0.5M) | 84.9 |
| 30.9 (1.8M) | 100 (1.0M) | 99.6 |
| 40.0 (2.4M) | 100 (1.0M) | 98.0 |
| 60.2 (3.5M) | 100 (1.0M) | 88.0 |
| 98.4 (5.8M) | 100 (1.0M) | 65.2 |

[1]Approximately 13.1 g/l Cu++ in the solution which can be characterized as a synthetic leach solution
[2]Concentration of the benzoxazole of Example III was 24.5% w/v (0.5M) in Napoleum 470, O/A = 1/1
[3]Total analyzable ammonia.

TABLE 10

Stripping of the Copper Loaded Benzoxazole[1] of Example III with Sulfuric Acid

| Strip Solution | | Stripped Organic |
|---|---|---|
| $H_2SO_4$ g/l | Cu++ g/l | Cu++ g/l |
| 25 | 40 | 10.4 |
| 25 | 0 | 9.7 |
| 50 | 40 | 4.9 |
| 50 | 0 | 4.6 |
| 75 | 40 | 0.9 |
| 75 | 0 | 0.9 |

[1]Contained about 18.3 g/l Cu, 0.0 g/l $NH_3$, O/A = 1/1.

TABLE 11

Selectivity of the Benzoxazole of Example III[1] For Copper, Nickel and Zinc

| | Organic | | Aqueous | |
|---|---|---|---|---|
| O/A | Cu++ g/l | Ni++ g/l | Cu++ g/l | Ni++ g/l |
| Feed[2] | 0.0 | 0.1 | 1.54 | 1.40 |
| 1/2 | 3.29 | 0.26 | 0.007 | 1.27 |
| 1/1 | 1.64 | 0.10 | 0.04 | 1.32 |
| 2/1 | 0.88 | 0.12 | 0.01 | 1.18 |
| | Cu++ g/l | Zn++ g/l | Cu++ g/l | Zn++ g/l |
| Feed[2] | 0.0 | 0.0 | 1.56 | 1.55 |
| 1/2 | 2.97 | 0.28 | 0.15 | — |
| 1/1 | 1.69 | 0.07 | 0.006 | 1.68 |
| 2/1 | 0.87 | 0.11 | 0.001 | 1.55 |

[1]About 5% w/v in Napoleum 470 (0.1M).
[2]Contained about 5 g/l $NH_3$ and 7 g/l $(NH_4)_2CO_3$.

EXAMPLE XIII

In the same manner as in Example VII, the kinetics of Ni and Cu Extraction was further studied using the benzoxazole of Example I. The results are seen in the following Table 12.

TABLE 12

Kinetics of Ni and Cu Extraction With the Benzoxazole of Example I[1]

| | Organic | | Aqueous[2] | |
|---|---|---|---|---|
| Time | Cu++ g/l | Ni++ g/l | Cu++ g/l | Ni++ g/l |
| 15 sec | 1.39 | 0.099 | 0.14 | 1.41 |
| 30 sec | 1.47 | 0.117 | 0.05 | 1.38 |
| 60 sec | 1.56 | 0.153 | 0.02 | 1.35 |
| 2 min | 1.55 | 0.213 | 0.005 | 1.22 |
| 5 min | 1.53 | 0.314 | 0.004 | 1.18 |

[1]An approximately 3.8% (0.1M) solution of the benzoxazole of Example I in Napoleum 470 was used.
[2]Aqueous Feed: 1.53 g/l Cu, 1.51 g/l Ni, 10 g/l $NH_3$, 7 g/l $(NH_4)_2CO_3$. O/A = 1/1

EXAMPLE XIII

The rate of nickel and copper extraction was similarly studied using the compound of Example III using an aqueous nickel feed of 2.8 g/l Ni and an aqueous copper feed of 3.2 g/l Cu. Both aqueous feed solutions also contained 5 g/l $NH_3$ and 7 g/l $(NH_4)_2CO_3$. The organic consisted of 4.9% w/v in Napoleum 470 of the compound of Example III and an O/A ratio of 1:1 was employed. The results are found in the following Table 13.

TABLE 13

Rate of Nickel and Copper Extraction

| | Nickel Concentration g/l Ni++ | | Copper Concentration g/l Cu++ | |
|---|---|---|---|---|
| Time | Organic | Aqueous | Organic | Aqueous |
| 15 sec | 0.34 | 2.71 | 0.83 | 2.20 |
| 30 sec | 0.39 | 2.57 | 1.24 | 1.84 |
| 60 sec | 0.48 | 2.53 | 1.72 | 1.23 |
| 2 min | 0.51 | 2.43 | 2.37 | 0.55 |
| 5 min | 0.52 | 2.43 | 2.82 | 0.04 |
| 10 min | 0.64 | 2.34 | 2.82 | 0.01 |

EXAMPLE XIV

In the same manner as the preceding examples, the extraction of nickel and copper was studied using the compound of Example II. The results can be seen from the following Table 14.

TABLE 14

Extraction of Nickel and Copper by 2-(2-Hydroxyphenyl)-5-hexylbenzoxazole[1]

| Aqueous Feed | [M][4] Organic | [M] Aqueous |
|---|---|---|
| 3.10 g/l Cu[2] | 2.73 g/l Cu++ | 0.27 g/l Cu++ |
| 3.35 g/l Ni[3] | 2.39 g/l Ni++ | 0.96 g/l Ni++ |

[1]0.1M solution in Napoleum 470
[2]Also contains 7 g/l $NH_3$, and 6 g/l $(NH_4)_2CO_3$. O/A = 1/1
[3]Also contains 7 g/l $NH_3$, and 6 g/l $(NH_4)_2CO_3$. O/A = 1/1.
[4]Calculated by difference.

EXAMPLE XV

In the same manner described in the earlier examples, studies were made using the benzoxazole of Example IV. The results can be seen from the following Tables 15 – 23.

TABLE 15

Extraction of Copper

| Time | Cu (org)[1] g/l | Cu (aq)[2] g/l |
|---|---|---|
| 15 sec | 2.64 | 0.29 |
| 30 sec | 2.75 | 0.21 |
| 60 sec | 2.75 | 0.22 |
| 2 min | 2.80 | 0.20 |
| 5 min | 2.68 | 0.22 |
| 10 min | 2.72 | 0.23 |

[1]Organic feed contained 0.1M (4.4 w/v %) of the benzoxazole of Example IV in Napoleum 470.
[2]Aqueous feed contained 2.90 g/l Cu++ as $CuSO_4$, 4.5 g/l $NH_3$ and 7.0 g/l $(NH_4)_2CO_3$. O/A = 1/1.

TABLE 16

Stripping of Copper

| Time | Cu (org)[1] g/l | Cu (aq)[2] g/l |
|---|---|---|
| 15 sec | 2.58 | 0.16 |
| 30 sec | 2.51 | 0.25 |
| 60 sec | 2.34 | 0.41 |
| 2 min | 2.05 | 0.69 |
| 5 min | 1.53 | 1.19 |
| 10 min | 0.95 | 1.85 |

[1]The organic feed contained 0.1M (4.4 w/v%) benzoxazole of Example IV and 2.74 g/l Cu++ in Napoleum 470.
[2]The aqueous feed contained 100 g/l $H_2SO_4$. O/A = 1/1.

TABLE 17

Kinetics of Stripping

| | With Catalyst | | Without Catalyst | |
|---|---|---|---|---|
| Time | Cu (org)[1] g/l | Cu (aq)[2] g/l | Cu (Org)[3] g/l | Cu (aq)[2] g/l |
| 15 sec | 1.77 | 0.85 | 2.58 | 0.16 |
| 30 sec | 1.38 | 1.16 | 2.51 | 0.25 |

TABLE 17-continued

| | Kinetics of Stripping | | | |
|---|---|---|---|---|
| | With Catalyst | | Without Catalyst | |
| Time | Cu (org)[1] g/l | Cu (aq)[2] g/l | Cu (Org)[3] g/l | Cu (aq)[2] g/l |
| 60 sec | 0.59 | 1.92 | 2.34 | 0.41 |
| 2 min | 0.20 | 2.65 | 2.05 | 0.69 |
| 5 min | 0.016 | 2.90 | 1.53 | 1.19 |
| 10 min | 0.017 | 2.92 | 0.95 | 1.85 |

[1]Organic contained 4% w/v of the benzoxazole of Example IV, 0.4% w/v of 5,8-diethyl-7-hydroxy dodecane-6-oxime and 2.50 g/l Cu++.
[2]Aqueous contained 100 g/l $H_2SO_4$. $O/A = 1/1$ [3]Organic contained 4% w/v of the benzoxazole of Example IV and 2.75 g/l Cu++

TABLE 18

Extraction of Ni[1] with the Benzoxazole of Example IV[2]

| O/A | Ni++ (org) g/l | Ni++ (aq) g/l |
|---|---|---|
| 1/5 | 2.75 | 2.35 |
| 1/2 | 2.72 | 1.48 |
| 1/1 | 2.72 | 0.21 |
| 2/1 | 1.48 | 0.0003 |
| 5/1 | 0.59 | 0.00005 |

[1]Aqueous feed contains 2.93 g/l Ni++, 6.8 g/l $(NH_4)_2CO_3$, and 7 g/l $NH_3$.
[2]Approximately 0.1M of the benzoxazole of Example IV (4.5% w/v) in Napoleum 470.

TABLE 19

Stripping of Ni from the Benzoxazole of Example IV[1]

| | Organic | | Aqueous | |
|---|---|---|---|---|
| O/A | Ni++ in Feed g/l | Ni++ in Stripped Organic g/l | $H_2SO_4$ in Feed g/l | Ni++ in P. E.[2] g/l | NH in P. E.[2] g/l |
| 1/1 | 13.5 | 11.3 | 25 | 2.2 | 4.9 |
| 1/2 | 13.5 | 8.3 | 25 | 2.6 | 2.5 |
| 1/1 | 13.5 | 7.8 | 50 | 5.7 | 4.9 |
| 1/1 | 13.5 | 6.0 | 75 | 7.5 | 5.1 |

[1]Approximately 0.5M (22.5% w/v) and maximum loaded with Ni from ammoniacal solution.
[2]Pregnant electrolyte - i.e. loaded strip solution.

TABLE 20

Kinetics of Ni[1] Extraction with The Benzoxazole of Example IV[2]

| Time | Ni++ (org) g/l | Ni++ (aq) g/l |
|---|---|---|
| 15 sec | 1.17 | 1.66 |
| 30 sec | 1.68 | 1.17 |
| 60 sec | 2.11 | 0.71 |
| 2 min | 2.47 | 0.41 |
| 5 min | 2.65 | 0.23 |
| 10 min | 2.66 | 0.20 |

[1]Contains 2.93 g/l Ni++, 6.7 g/l $(NH_4)_2CO_3$, and 7 g/l $NH_3$.
[2]Approximately 0.1M of the benzoxazole of Example IV (4.5% w/v) in Napoleum 470. O/A = 1/1.

TABLE 21

Kinetics of Ni Stripping from Ni Loaded Organic[1]

| Time | Ni++ (org) g/l | Ni++ (aq) g/l |
|---|---|---|
| 15 sec | 2.52 | 0.14 |
| 30 sec | 2.42 | 0.22 |
| 60 sec | 2.19 | 0.37 |
| 2 min | 2.00 | 0.59 |
| 5 min | 1.52 | 1.00 |
| 10 min | 0.90 | 1.57 |

[1]Aqueous feed contained 100 g/l $H_2SO_4$. Organic feed contained 2.67 g/l Ni++ in a 0.1M (4.5% w/v) solution of the benzoxazole of Example IV in Napoleum 470. O/A = 1/1.

TABLE 22

EFFECT OF CATALYST ON NICKEL EXTRACTION[1] (E) AND STRIPPING[2] (S) WITH THE BENZOXAZOLE OF EXAMPLE IV

| | No Catalyst[3] | | With Catalyst[4] | |
|---|---|---|---|---|
| Time[5] | % E | % S | % E | % S |
| 15 sec | 44 | 5 | 46 | 19 |
| 30 sec | 63 | 9 | 59 | 16 |
| 60 sec | 79 | 14 | 79 | 33 |
| 2 min | 93 | 23 | 97 | 52 |
| 5 min | 100 | 39 | 100 | 100 |
| 10 min | 100 | 61 | 100 | 100 |

[1]Aqueous feed for extraction contained 2.93 g/l Ni++ as $NiSO_4$, 6.7 g/l $(NH_4)_2CO_3$, and 7 g/l $NH_3$.
[2]Aqueous feed for stripping contained 100 g/l $H_2SO_4$
[3]Organic contained 4% (w/v) compound of Example IV in Napoleum 470. [4]Organic as above plus 0.4% (w/v) 5,8-diethyl-7-hydroxydodecane-6-oxime.
[5]All O/A ratios were 1/1.

TABLE 23

Zinc[1] Extraction With The Benzoxazole of Example IV[2]

| O/A | Zn++ (org) g/l | Zn++ (aq) g/l |
|---|---|---|
| 1/5 | 2.00 | 2.98 |
| 1/2 | 2.03 | 2.18 |
| 1/1 | 1.85 | 1.35 |
| 2/1 | 1.25 | 0.15 |
| 5/1 | 0.655 | 0.019 |

[1]Aqueous feed contained 2.3 g/l Zn++ as $ZnSO_4$, 7 g/l $NH_3$ and 6 g/l $(NH_4)_2CO_3$.
[2]Reagent concentration was 0.1M (4% w/v) in Napoleum 470.

EXAMPLE XVI

In this example the extraction and stripping of copper using the benzoxazole of Example V was conducted in the same manner as in the earlier examples herein. The results can be seen from the following Tables 24 – 26.

TABLE 24

Extraction of Copper[1] With 2-(2-Hydroxyphenyl)-5-Nonylbenzoxazole[2]

| O/A | Cu++ (org) g/l | Cu++ (aq) g/l |
|---|---|---|
| 1/5 | 3.08 | 2.44 |
| 1/2 | 3.03 | 1.61 |
| 1/1 | 2.95 | 0.21 |
| 2/1 | 1.60 | 0.0006 |
| 5/1 | 0.64 | 0.0002 |

[1]Aqueous feed contained 3.1 g/l Cu++ as $CuSO_4$, 7 g/l $NH_3$, and 6 g/l $(NH_4)_2CO_3$.
[2]Organic contained 0.1M (3.4% w/v) reagent in Napoleum 470.

TABLE 25

Stripping of Copper Loaded 2-(2-Hydroxyphenyl)-5-Nonylbenzoxazole[1]

| | Cu++ (g/l) | | $NH_3$ (g/l) |
|---|---|---|---|
| $H_2SO_4$ | Loaded Organic | Stripped Organic | Pregnant Strip Solution |
| 50 | 5.65 | 0.004 | 0.02 |
| 75 | 5.65 | 0.003 | 0.03 |
| 100 | 5.65 | 0.002 | 0.06 |

[1]Organic contained 0.2M (6.7 w/v %) reagent in Napoleum 470. O/A = 1/1.

TABLE 26

Kinetics of Copper Extraction and Stripping With 2-(2-Hydroxyphenyl)-5-Nonylbenzoxazole

| | Extraction | | Stripping | |
|---|---|---|---|---|
| Time | Cu++[1] (org) g/l | Cu++[2] (aq) g/l | Cu++[1] (org) g/l | Cu++[3] (aq) g/l |
| Start | 0.00 | 3.23 | 2.67 | 0.00 |

TABLE 26-continued

Kinetics of Copper Extraction and Stripping With 2-(2-Hydroxyphenyl)-5-Nonylbenzoxazole

| Time | Extraction | | Stripping | |
|---|---|---|---|---|
| | Cu++¹ (org) g/l | Cu++² (aq) g/l | Cu++¹ (org) g/l | Cu++³ (aq) g/l |
| 15 sec | 2.90 | 0.42 | 0.48 | 2.08 |
| 30 sec | 2.98 | 0.25 | 0.0014 | 2.60 |
| 1 min | 3.05 | 0.17 | 0.0027 | 2.80 |
| 2 min | 3.03 | 0.16 | 0.0003 | 2.71 |
| 5 min | 3.05 | 0.17 | 0.0005 | 2.70 |
| 10 min | 3.05 | 0.17 | 0.0020 | 2.70 |

¹Contained 0.1M (3.4% w/v) of reagent in Napoleum 470. All O/A ratios =1/1.
²Contained 7 g/l NH₃ and 6 g/l (NH₄)₂CO₃.
³Contained 100 g/l H₂SO₄.

EXAMPLE XVII

For comparative purposes 2-(2-hydroxyphenyl)-5-t-butylbenzoxazole was prepared. This derivative was found to have poor solubility at 2.5% (w/v) in the Napoleum 470 kerosene. This solubility could be improved by using 10% w/v isodecanol in Napoleum 470 as a diluent. During the course of attempted copper extractions from ammoniacal solutions, precipitates were encountered which appeared to be copper-benzoxazole complexes. In view of the precipitate formation the t-butyl derivative would be unsatisfactory as an extractant reagent for copper.

Similarly the unsubstituted compound, 2-(2-hydroxy-phenyl)-benzoxazole, was also investigated. Upon shaking 0.1M solutions (2.1% w/v) in Napoleum 470 with ether copper or nickel ammoniacal solutions, large amounts of deeply colored precipitates formed. Thus, while metal chelates may form, such chelates appear to be insoluble in Napoleum 470, one of the suitable solvents for use in extraction processes. In view of this insolubility, the unsubstituted material would be unsatisfactory as a commercially practical extractant reagent.

The embodiments of the invention in which an exclusive property or privilege is claimed are defined as follows:

1. A compound of the structure

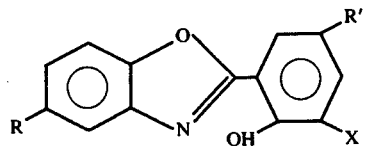

where R is hydrogen or alkyl having from 1 to 20 carbon atoms, R' is hydrogen, chlorine or alkyl having from 1 to 20 carbon atoms, X is hydrogen or chlorine, the total number of carbon atoms in R and R' is 6 to 40 and one of R and R' must be alkyl of at least 6 carbon atoms.

2. A compound as defined in claim 1 wherein R is alkyl of 9 or more carbon atoms and R' and X are hydrogen.

3. A compund as defined in claim 1 wherein R is dodecyl.

4. A compound as defined in claim 3 wherein R' is octyl.

5. A compound as defined in claim 1 wherein R is nonyl.

6. A compound as defined in claim 1 wherein R is hexyl.

7. 2-(2-Hydroxyphenyl)-5-dodecylbenzoxazole.
8. 2-(2-Hydroxyphenyl)-5-hexylbenzoxazole.
9. 2-(2-Hydroxyphenyl)-5-nonylbenzoxazole.
10. 2-(2-Hydroxy-5-octylphenyl)-5-dodecylbenzoxazole.
11. 2-(2-Hydroxy-3,5-dichlorophenyl)-5-dodecylbenzoxazole.

* * * * *

UNITED STATES PATENT AND TRADEMARK OFFICE
CERTIFICATE OF CORRECTION

PATENT NO. : 4,020,081
DATED : April 26, 1977
INVENTOR(S) : Kenneth D. MacKay & Edgar R. Rogier It is certified that error appears in the above-identified patent and that said Letters Patent are hereby corrected as shown below:

Column 2, Line 20: "alos" should read -- also --;
          Line 23: "inention" should read -- invention --.
Column 3, Line 11: After "R" insert -- is --;
          Line 33: After "organic" insert -- phase --;
          Line 34: After "pressure." insert -- Further --;
          delete "distillation" in the second instance;
          Line 45: "stopped" should read -- stoppered --;
          Line 63: delete "the" in the first instance.

Column 5, Line 48: "152" should read -- 153 --.

Column 10, Line 54: "Example III$^1$" should read -- Example III$^2$ --

Column 15, Line 32: "ether" should read -- either --.

Signed and Sealed this

Tenth Day of January 1978

[SEAL]

Attest:

RUTH C. MASON
Attesting Officer

LUTRELLE F. PARKER
Acting Commissioner of Patents and Trademark